(12) United States Patent
Hewson et al.

(10) Patent No.: US 11,045,608 B2
(45) Date of Patent: Jun. 29, 2021

(54) INJECTION DEVICE WITH DOSE INDICATOR MECHANISM

(71) Applicant: NORTON HEALTHCARE LIMITED, West Yorkshire (GB)

(72) Inventors: Karl James Hewson, Cambridgeshire (GB); George Bostock, Cambridgeshire (GB); George Robert Michael Savell, Cambridgeshire (GB)

(73) Assignee: Norton Healthcare Limited, Castleford (GB)

( * ) Notice: Subject to any disclaimer, the term of this patent is extended or adjusted under 35 U.S.C. 154(b) by 146 days.

(21) Appl. No.: 16/332,051

(22) PCT Filed: Sep. 11, 2017

(86) PCT No.: PCT/EP2017/072724
§ 371 (c)(1),
(2) Date: Mar. 11, 2019

(87) PCT Pub. No.: WO2018/046722
PCT Pub. Date: Mar. 15, 2018

(65) Prior Publication Data
US 2019/0262546 A1    Aug. 29, 2019

(30) Foreign Application Priority Data
Sep. 12, 2016  (GB) ...................................... 1615450

(51) Int. Cl.
*A61M 5/31*        (2006.01)
*A61M 5/315*       (2006.01)
(Continued)

(52) U.S. Cl.
CPC .......... *A61M 5/31551* (2013.01); *A61M 5/20* (2013.01); *A61M 5/31536* (2013.01);
(Continued)

(58) Field of Classification Search
CPC .......... A61M 5/31551; A61M 5/31553; A61M 5/31583; A61M 5/20; A61M 5/31536;
(Continued)

(56) References Cited

U.S. PATENT DOCUMENTS

| 5,279,585 A | * | 1/1994 | Balkwill | ............ | A61M 5/3158 |
| | | | | | 222/309 |
| 8,672,898 B2 | | 3/2014 | Enggaard | | |
| 2007/0021715 A1 | * | 1/2007 | Kohlbrenner | ........... | A61M 5/20 |
| | | | | | 604/67 |

FOREIGN PATENT DOCUMENTS

| EP | 0554995 A1 | 8/1993 |
| FR | 2531879 A1 | 2/1984 |

(Continued)

OTHER PUBLICATIONS

International Search Report and Written Opinion, PCT/EP2017/072724, dated Dec. 11, 2017, 17 pages.

*Primary Examiner* — Theodore J Stigell
*Assistant Examiner* — Daniel Moore
(74) *Attorney, Agent, or Firm* — BakerHostetler

(57) ABSTRACT

An injection device comprises a housing (12) having a longitudinal axis. The injection device further comprises a dose selector (16) capable of setting a dose to be ejected from the injection device and a dose indicator comprising a units wheel (18) operatively connectable to the dose selector so that rotation of the dose selector about the longitudinal axis also rotates the units wheel, and a tens wheel (19) selectively engageable with the units wheel so that rotation of the units wheel also rotates the tens wheel. A biasing means biases the dose indicator axially-rearwardly in the housing. An internal surface of the housing is provided with a tens housing feature selectively engageable with the tens wheel to prevent rotation thereof. An internal surface of the housing is provided with a units housing feature capable of (Continued)

moving the units wheel axially-forward against said biasing means such that the units wheel engages and moves the tens wheel axially-forward and free of said tens housing feature so as to allow rotation thereof.

13 Claims, 18 Drawing Sheets

(51) Int. Cl.
 *A61M 5/20* (2006.01)
 *A61M 5/24* (2006.01)
(52) U.S. Cl.
 CPC .... *A61M 5/31553* (2013.01); *A61M 5/31583* (2013.01); *A61M 5/24* (2013.01); *A61M 5/3129* (2013.01); *A61M 5/3157* (2013.01); *A61M 5/31511* (2013.01); *A61M 5/31535* (2013.01); *A61M 5/31541* (2013.01); *A61M 5/31593* (2013.01); *A61M 2005/3126* (2013.01); *A61M 2005/3154* (2013.01)

(58) Field of Classification Search
 CPC ............... A61M 5/24; A61M 5/31535; A61M 5/31593; A61M 5/3129; A61M 5/3157; A61M 5/31541; A61M 5/31511; A61M 2005/3126; A61M 2005/3154
 See application file for complete search history.

(56) References Cited

FOREIGN PATENT DOCUMENTS

| | | | |
|---|---|---|---|
| WO | 2006/045528 | A1 | 5/2006 |
| WO | 2013/087574 | A1 | 6/2013 |
| WO | 2013/178372 | A1 | 12/2013 |
| WO | 2014/166908 | A1 | 10/2014 |
| WO | 2014/166909 | A1 | 10/2014 |
| WO | 2015/007819 | A1 | 1/2015 |
| WO | 2015/007820 | A1 | 1/2015 |
| WO | 2015/181141 | A1 | 12/2015 |
| WO | 2016/055438 | A1 | 4/2016 |

* cited by examiner

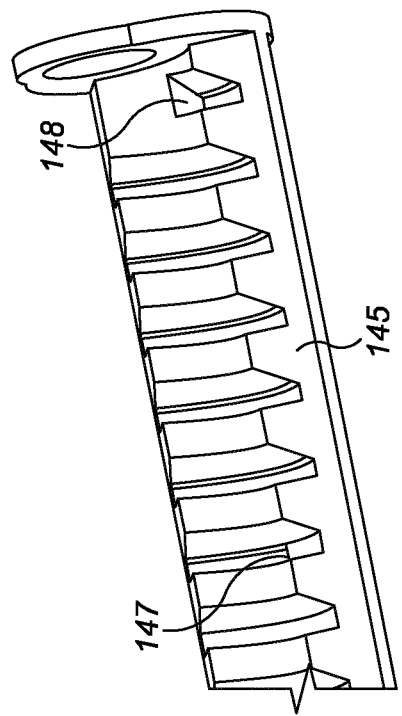
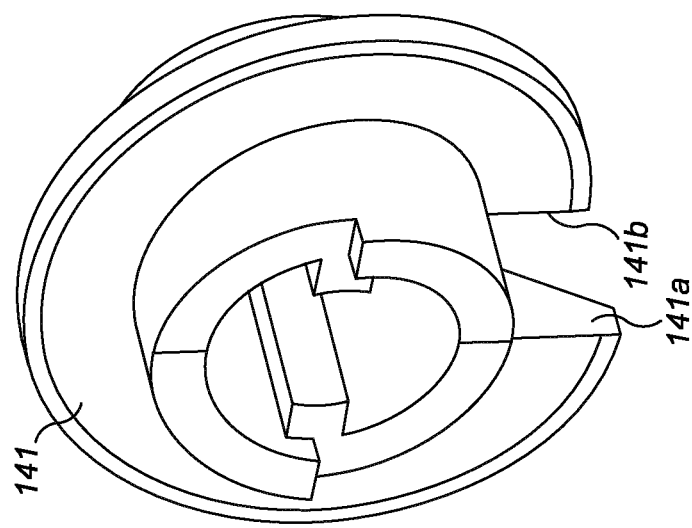
FIG. 5B
FIG. 5A

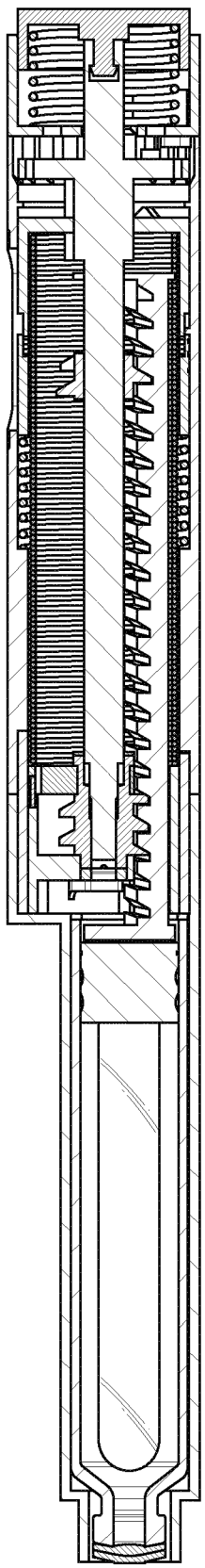
FIG. 13
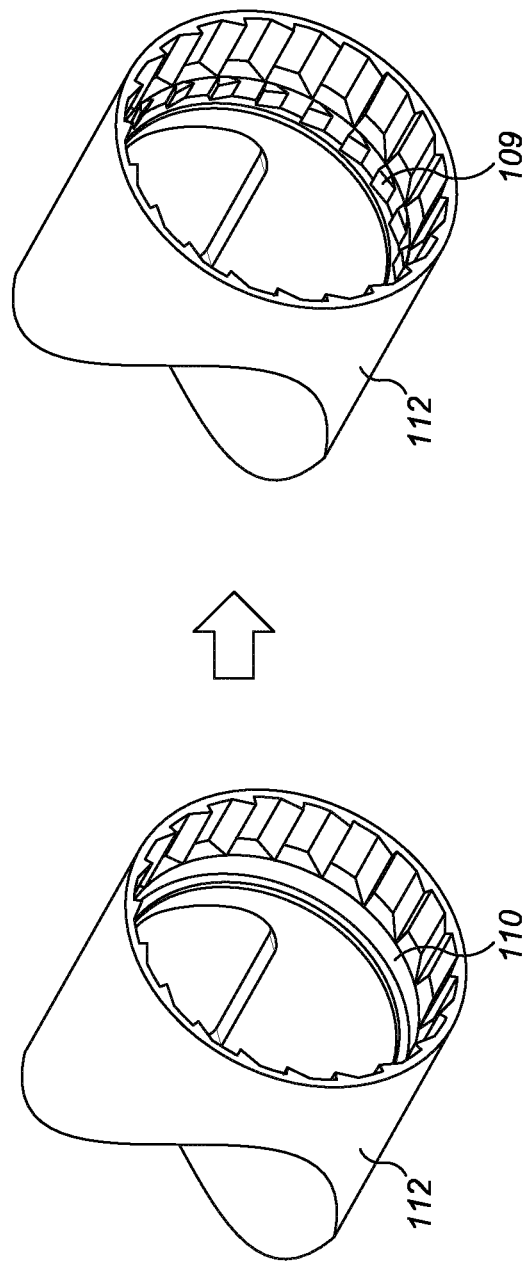
FIG. 13A
FIG. 13B

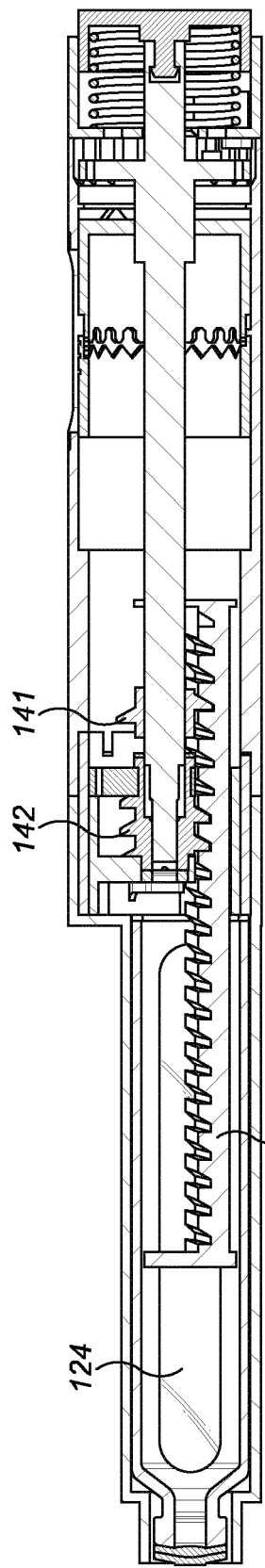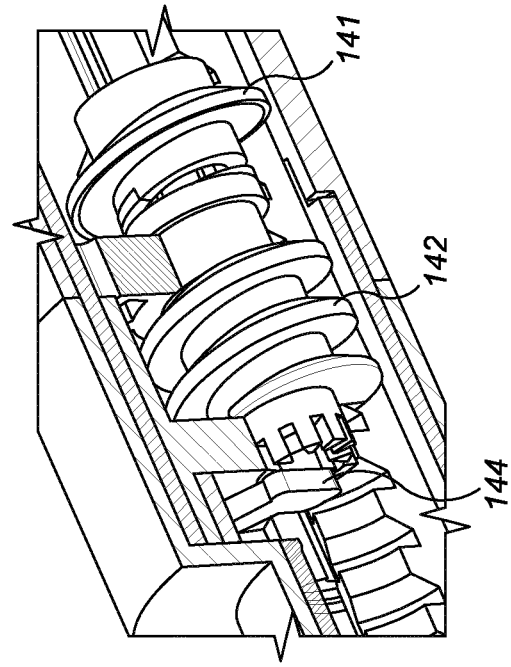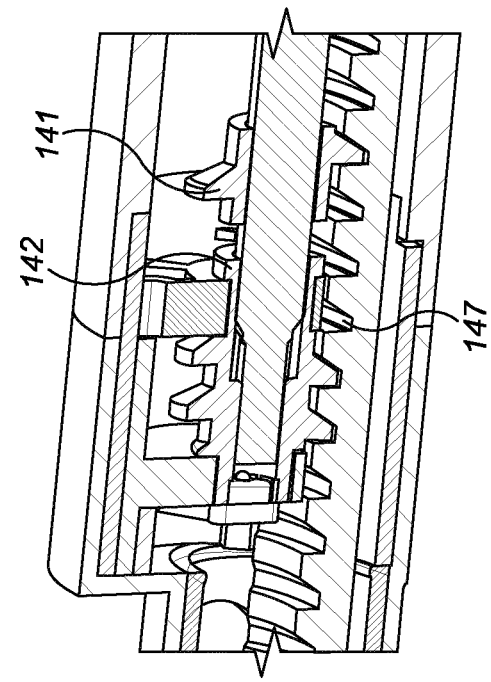

| Advancement of dose button (130) in mm | 0mm | 0.9mm | 1.75mm | 3.25mm |
|---|---|---|---|---|
| Hold Ratchet (Housing ramp 111/ Ratchet Arms (146)) | Not Engaged | Partially Engaged | Fully Engaged | Fully Engaged |
| Over torque ratchet (drive torque ratchet (drive shaft spline (149)/dose selector pawl (115)) | Not Engaged | Partially Engaged | Fully Engaged | Fully Engaged |
| Worm Gear Clutch (150) | Not Engaged | Fully Engaged | Fully Engaged | Fully Engaged |
| Worm Gear Rotational Lock (144) | Not Engaged | Partially Engaged | Fully Engaged | Fully Engaged |

FIG. 15

INJECTION DEVICE WITH DOSE INDICATOR MECHANISM

CROSS-REFERENCE TO RELATED APPLICATIONS

This application is the National Stage of International Patent Application No. PCT/EP2017/072724, filed Sep. 11, 2017, which claims priority from Great Britain Patent Application No. 1615450.2, filed Sep. 12, 2016, the entire contents of both of which applications are incorporated herein by reference.

This disclosure relates to the field of a dose indicator mechanism for an injection device, preferably having a torsion spring for assisting injection of a dose of medicament from the injection device.

BACKGROUND

Certain injection devices are required to have a visual indicator for the user so that the correct dose of medicament can be set and observed. This dose indicator commonly takes the form of a number sleeve, an example of which is described in U.S. Pat. No. 8,672,898. A rotatable sleeve with numbers printed along a helical line can be inspected through a window in the housing of the device, the window showing only one of the numbers at a time which corresponds to the dose set. However, U.S. Pat. No. 8,672,898 uses a linear compression spring. An example of a number sleeve in an injection device using a torsion spring is described in WO2014/166908.

A disadvantage of using a number sleeve to indicate the dose is that the indicator area takes up a relatively large portion of the device and is generally centrally located, as illustrated in FIG. 2 of WO2014/166908. Desirably, the dose indicator needs to avoid areas of the device where the user will grip the device, so that the user's fingers do not obscure the dose indication.

An alternative type of dose indication is provided by an odometer or "units and tens" wheels or ciphers arrangement in place of a number sleeve. An example is given in WO2006/045528. Two wheels, each carrying the ten ciphers from "0" to "9" are used wherein the "tens" wheel is rotated one increment every time the "units" wheel is rotated one full revolution so that the two wheels between them can form all of the numbers from "00" to "99" in a display window. An odometer has an advantage over a number sleeve as a dose indicator in that it can be located further rearwardly towards the proximal end of the device where it is less likely to interfere with the user's finger position.

In WO2006/045528, when the dose setting member is rotated, a torsion spring is charged or strained, ready to deliver the appropriate dose. At the same time, and in parallel, the display wheels can be rotated by a planet gear 17 to display the dose which has been set.

U.S. Pat. No. 5,279,585 describes a medication delivery pen having a units counter ring and a tens counter ring. The units counter ring is splined to an axially-moveable plunger and is also secured to a dose adjusting knob such that rotation of the dose adjusting knob causes a corresponding rotation of the units counter ring. Grooves on the tens counter ring are engageable with a zero detection clip. A transmission key is provided on the units counter ring for engaging and disengaging the units and tens counter rings together.

WO2013/087574 describes another example of an injector pen having an odometer, in the form of two different scale drums rotatably mounted with respect to the housing of the injection device and moveable axially with respect to the housing when rotated.

BRIEF SUMMARY OF THE DISCLOSURE

In accordance with an aspect of the present invention there is provided an injection device comprising:
  a. a housing having a longitudinal axis;
  b. a dose selector capable of setting a dose to be ejected from the injection device;
  c. a dose indicator comprising a units wheel operatively connectable to the dose selector so that rotation of the dose selector about the longitudinal axis also rotates the units wheel, and a tens wheel selectively engageable with the units wheel so that rotation of the units wheel also rotates the tens wheel; and
  d. a biasing means for biasing the dose indicator axially-rearwardly in the housing,
  wherein an internal surface of the housing is provided with a tens housing feature selectively engageable with the tens wheel to prevent rotation thereof, and wherein an internal surface of the housing is provided with a units housing feature capable of moving the units wheel axially-forward against said biasing means such that the units wheel engages and moves the tens wheel axially-forward and free of said tens housing feature so as to allow rotation thereof.

By providing features in the housing for both the tens wheel and units wheel to engage with, the accuracy of the dose indicator may be improved. In particular, by having the tens wheel normally engaged with the housing so that it cannot rotate, the risk of the tens wheel moving unintentionally is reduced. The tens wheel is temporarily disengaged from the tens housing feature by the units wheel only when it is required for the tens wheel to increment and then the tens wheel is re-engaged with the tens housing feature until next required.

In an embodiment, the biasing means is a spring.

In an embodiment, the units housing feature comprises a cam surface.

Preferably, the units wheel comprises an axially-rearwardly-extending formation for engaging said cam surface on the housing.

In certain embodiments, the tens housing feature comprises one or more formations with corresponding formations on said tens wheel.

In certain embodiments, said units wheel is selectively engageable with said tens wheel by means of one or more teeth on the units wheel engageable with corresponding teeth on said tens wheel.

The formations and/or teeth may be regularly spaced.

The formations and/or teeth on the tens wheel may be located at a rear end of said tens wheel.

Said tens wheel teeth for engaging the units wheel may be located radially inwardly of the tens wheel formations for engaging the tens housing feature.

Preferably, the dose indicator is arranged concentrically about said longitudinal axis.

The injection device may further comprise a medicament container. The medicament container may comprise a prefilled syringe or cartridge. Medicament may be contained in the medicament cartridge. In certain embodiments, the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIG. 5A is a perspective view showing further detail of the dose limit nut;

FIG. 5B is a perspective view showing further detail of part of the plunger rack;

FIGS. 11,11A-110, 12 and 12A-12B illustrate dose delivery;

FIGS. 13, 13A and 13B illustrate a haptic feedback feature;

FIGS. 14 and 14A-14E illustrate last dose protection;

FIG. 15 is a diagrammatic summary of the key engagement points of the components of the injection device of FIG. 4, at four stages of dose delivery;

DETAILED DESCRIPTION

Figure 1:
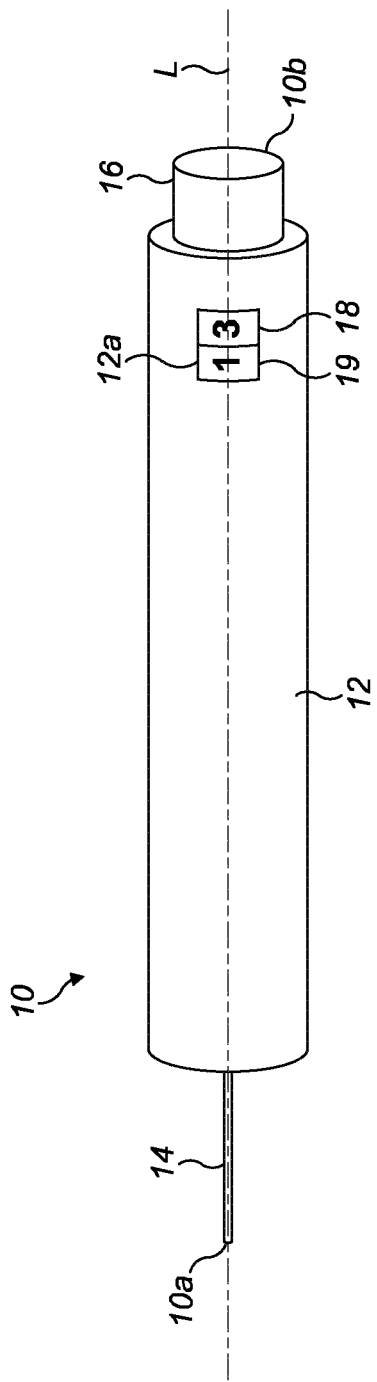
FIG. 1 shows an injection device in accordance with an embodiment of the present invention.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components.

The term "a rotational coupling" may refer to a coupling which enables a rotational force to be transmitted between the components.

The term "operatively connectable" may refer to at least two individual components which are releasably connectable together in such a way that the individual components can work together, for example wherein rotation of one of the individual components effects rotation of all of the operatively connected components.

The term "dose selector" may refer to a component or components which, when actuated by a user, enable a dose of medicament to be selected.

The term "dose indicator" may refer to a component or components which provide a display or indication to the user of the selected dose of medicament.

The term "splines" may refer to one or more ridges, ribs or other protrusions on one component which engage in corresponding grooves or the like on a second component to connect the two components together.

The term "a splined connection" may refer to a connection effected by one or more splines.

The term "forward" or "forwards" may refer to a direction towards the end of the injection device from which medicament is expelled.

The term "backward", "backwards", "rearward" or "rearwardly" may refer to a direction away from the end of the injection device from which medicament is expelled.

The term "drive assembly" may refer to an assembly of components capable of using a driving force from, for example, a spring, to eject medicament from an injection device.

The term "backlash" may refer to a clearance caused by a gap between mechanical components.

The term "medicament" may include a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament" may refer to the medicament being contained within a suitable medicament container, such as a pre-filled syringe or cartridge, within the injection device.

The term "a force path" may refer to a path between two or more coupled components via which a force can be transmitted between the components. A force path may be "interrupted" if there is a gap between the two or more components, i.e. if they are no longer coupled. Transmission of force between coupled components may be "held back" for example by a ratchet arrangement, but in such a case the force path is not "interrupted".

The term "a clutch" may refer to a component or feature suitable for operatively connecting two component parts either by a positive fit e.g. with teeth, splines, grooves or the like suitable for engaging and disengaging each other, or by a non-positive (e.g. frictional) connection or a combination thereof. Disengaging the clutch may interrupt a force path between two or more coupled components.

Description of a First Example Embodiment

An injection device 10 according to an embodiment of the present invention is shown in FIG. 1. The injection device 10 is configured to deliver a dose of medicament and extends along a longitudinal axis L between a front end 10a and a rear end 10b of the injection device 10. The injection device 10 has a housing 12 and a needle 14 projecting from the housing 12 at the front end 10a. A dose selector 16 is provided at the rear end 10b and is arranged to permit the selection of a desired dose of medicament for delivery through the needle 14 into an injection site. The housing 12 includes an aperture 12a through which a dose indicator is visible.

The dose indicator is disposed within the housing 12 and displays reference indicia, such as numbers or symbols, to indicate the level of dose selected by the dose selector 16. The dose indicator may be an odometer which may include a plurality of parts for indicating individual orders of magnitude of the selected dose. For example, the odometer may comprise a units wheel 18 for displaying units and a tens wheel 19 for displaying tens. The units wheel may be selectively engageable with the tens wheel to increment the tens wheel each time the units wheel moves through units 0 to 9.

In the preferable but non-limiting embodiment shown in FIG. 1, the aperture 12a is provided towards the rear end 10b of the injection device 10 so that the dose indicator remains visible when the injection device 10 is handled by a user. The aperture 12a (and underlying dose indicator) may be provided elsewhere on the injection device 10 in alternative embodiments. Similarly, the dose selector 16 is shown in FIG. 1 disposed at the rear end 10b of the injection device 10 and this may be advantageous insofar as being clear of the region of the housing 12 that is likely to be gripped by a user during use of the injection device 10. In other embodiments, the dose selector 16 may be provided elsewhere.

Figure 2:
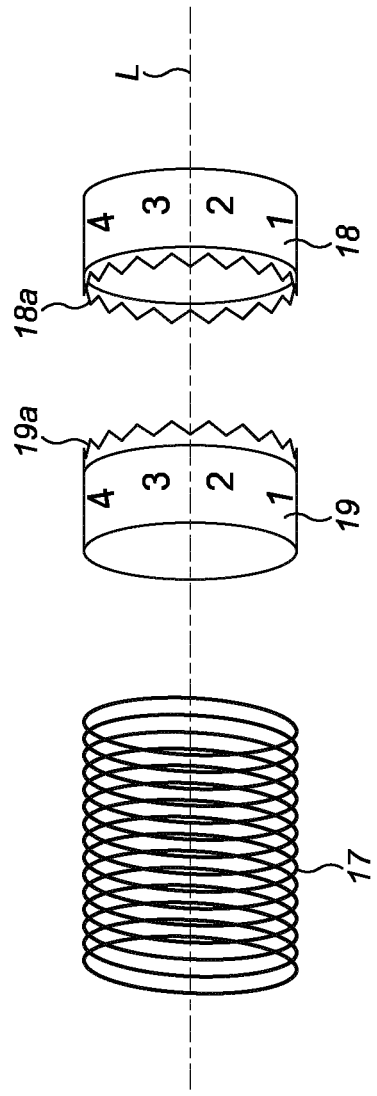
FIG. 2 is an exploded view of selected components of the injection device of FIG. 1 along the longitudinal axis L.

FIG. 2 shows an exploded view of the dose indicator comprising a units wheel 18 and tens wheel 19 arranged along the longitudinal axis L. A biasing means in the form of a dose indicator spring 17 is provided for biasing the dose indicator axially-rearwardly in the housing 12 (not shown in FIG. 2). The units wheel 18 and tens wheel 19 are rotatable about the longitudinal axis L and are selectively engageable together by means of teeth 18a, 19a respectively. Engagement between the first plurality of teeth 18a and second plurality of teeth 19a forms a rotational coupling to operatively connect the units wheel 18 to the tens wheel 19 such that torque may be transferred therebetween.

Figure 3:
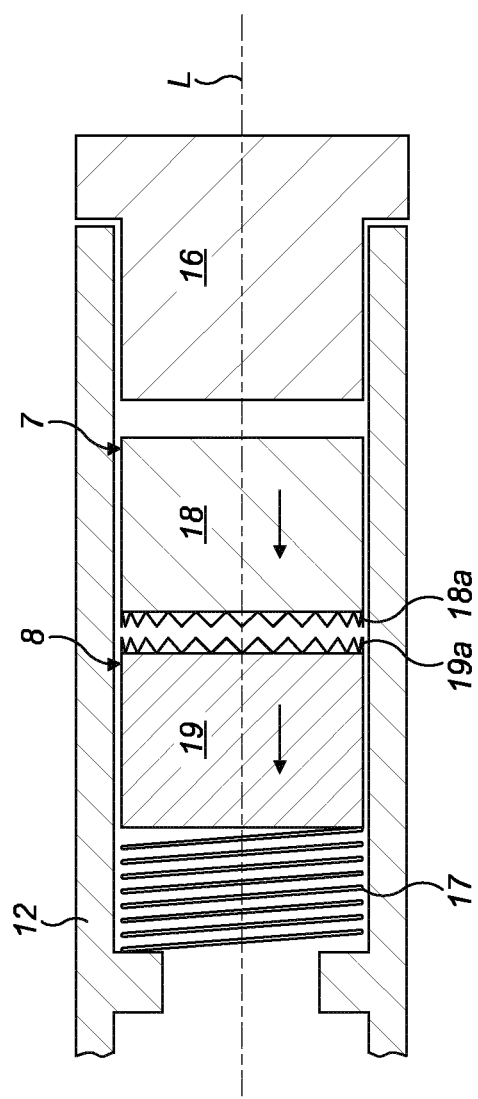
FIG. 3 is a schematic representation of selected components of the injection device of FIG. 1.

FIG. 3 is a schematic representation of selected components of the injection device 10 arranged around the longitudinal axis L. The dose selector 16 is operatively connected to the units wheel 18 such that rotation of the dose selector 16 about the longitudinal axis L also rotates the units wheel 18.

The tens wheel 19 is selectively engageable with the units wheel 18 via teeth 18a, 19a, as described above. When the units wheel 18 and tens wheel 19 are engaged, rotation of the units wheel 18 also rotates the tens wheel 19.

An internal surface of the housing 12 is provided with a units housing feature 7 wherein, when the units wheel 18 is rotated into contact with the units housing feature 7, the units housing feature 7 causes (for example by the action of a cam surface) forward axial movement of the units wheel 18, in the direction indicated by the arrow in FIG. 3.

An internal surface of the housing 12 is provided with a tens housing feature 8 which is normally engaged with the tens wheel 19 to prevent rotation thereof. When the units wheel 18 moves axially forwards as indicated in FIG. 3, it engages with the tens wheel 19 via the teeth 18a, 19a. Continued forward axial movement of the units wheel 18 causes corresponding forward axial movement of the tens wheel 19, as indicated by the arrow in FIG. 3. Sufficient forward axial movement of the tens wheel 19 causes the tens wheel 19 to disengage from the tens housing feature 8. Once free of the tens housing feature 8, the tens wheel 19 is free to rotate in order to increment the tens indicated by the dose indicator.

When the units wheel 18 has been rotated past the units housing feature 7, the units wheel 18 is no longer urged axially forward. Both the units wheel 18 and the tens wheel 19 return to their initial positions because of the bias of the dose indicator spring 17. Back in its initial position, the tens wheel 19 re-engages the tens housing feature 8 so that it is rotationally locked with respect to the housing 12.

Description of Second Example Embodiment

A further, non-limiting, embodiment of an injection device according to the present invention is illustrated in FIGS. 4-19B.

Figure 4:
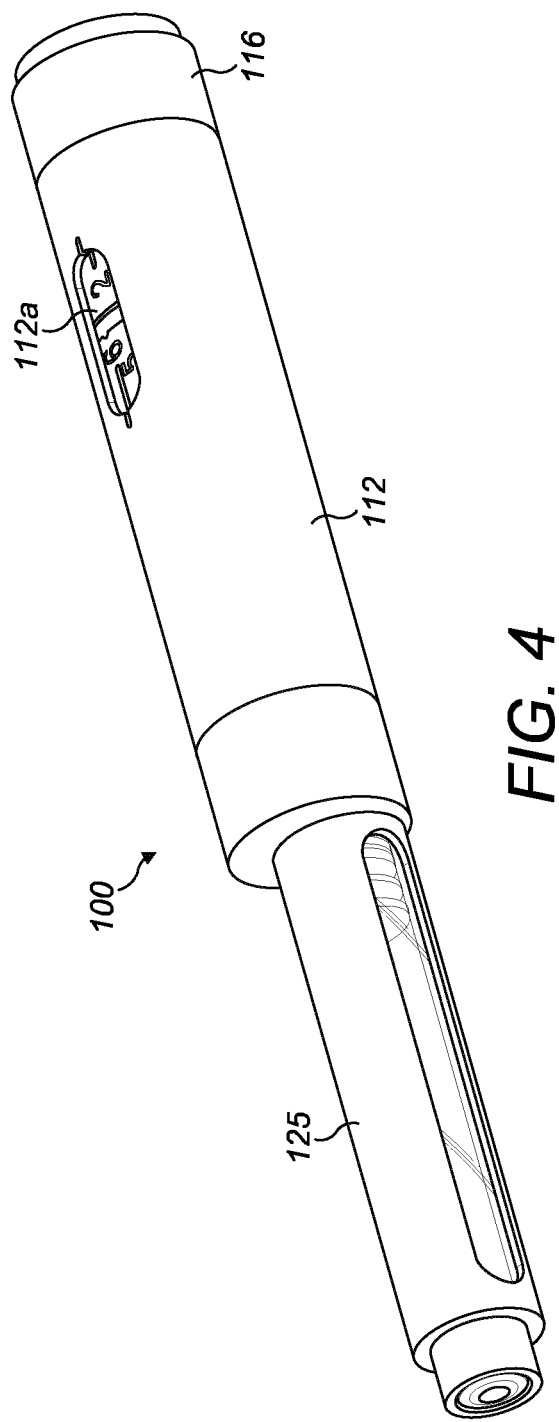
FIG. 4 is a perspective view of another embodiment of the injection device.
Figure 5:
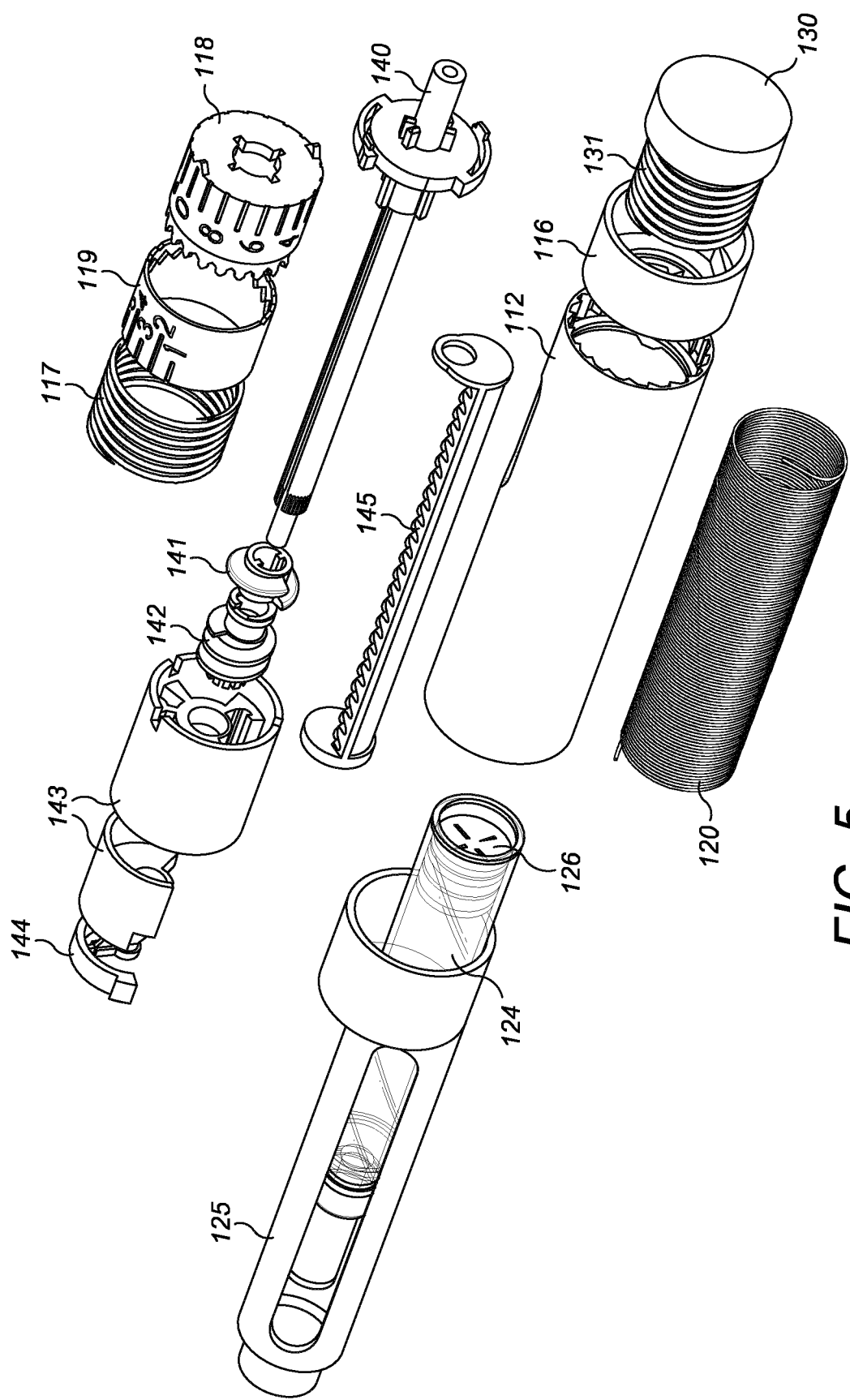
FIG. 5 is an exploded view of the injection device of FIG. 4.
Figure 6:
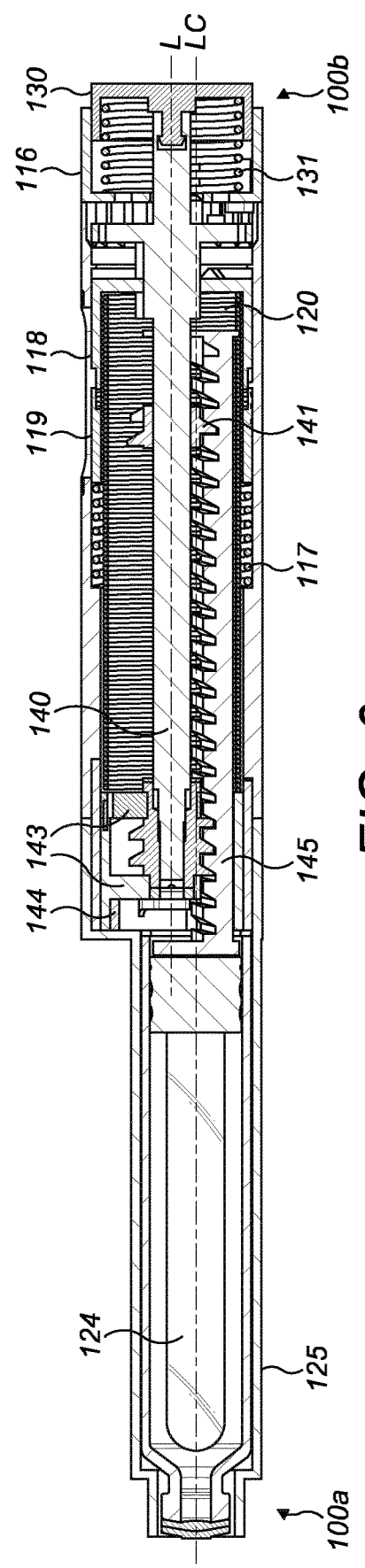
FIG. 6 is a cross-sectional view of the injection device of FIG. 4.

Referring to FIGS. 4-6, the injection device 100 includes a housing 112, a dose selector 116, a dose button 130 and dose button spring 131, a units wheel 118, a tens wheel 119, a dose indicator spring 117, a drive shaft 140, a drive spring 120, a dose limit nut 141, a worm gear 142, a worm gear support 143 and a worm gear rotational lock 144, all located concentrically about a common longitudinal axis L. The axis L extends between a front end 100a and a rear end 100b of the injection device 100.

The injection device 100 has a medicament cartridge 124 supported in a cartridge holder 125 at the front end 100a of the injection device 100. The cartridge 124 is sealed by an axially-moveable cartridge stopper 126 at its rear end. The cartridge and cartridge holder are located concentrically about a second longitudinal axis Lc, such that the cartridge is offset from the main housing 112, with L and Lc offset from one another as shown in FIG. 6.

The dose button 130 is biased rearwardly by the dose button spring 131. The dose selector 116 is provided at the rear end 100b of the injection device 100 and is arranged to permit the selection of a desired dose of medicament for delivery from the medicament cartridge 124 into an injection site. The dose selector 116 is axially constrained with respect to the housing 112 but is rotatable with respect thereto, about axis L. The dose selector 116 is rotationally coupled to the drive shaft 140 via pawl features 115, visible in FIG. 7A, which engage splines 149 on the drive shaft 140. The housing 112 is provided with teeth 113 (visible in FIG. 7B) on an inside surface thereof for engaging ratchet arms 146 on the drive shaft 140. Tabs 114 on the dose selector 116 are capable of depressing the drive shaft ratchet arms 146 when required, as shown in FIG. 8B. The housing 112 is also provided with ramp features 111 (visible in FIG. 12A) which facilitate disengagement of the ratchet arms 146 from the inside surface of the housing 112 when required.

A dose indicator is disposed within the housing 112 and displays reference indicia, such as numbers or symbols, to indicate the level of dose selected by the dose selector 116. The housing 112 includes an aperture 112a through which the dose indicator is visible. The dose indicator comprises the units wheel 118 for displaying units and the tens wheel 119 for displaying tens. The units wheel 118 is selectively engageable with the tens wheel to increment the tens wheel each time the units wheel moves through units 0 to 9. The units wheel 118 is rotationally coupled to the drive shaft 140.

As with the first embodiment, described with reference to FIGS. 1-3, biasing means in the form of dose indicator spring 117 biases the units wheel 118 and tens wheel 119 axially rearwardly in the housing.

The housing 112 has features on an inside surface thereof for engaging with the units wheel 118 and the tens wheel 119.

An internal surface of the housing 112 is provided with a tens housing feature 108 selectively engageable with the tens wheel 119 to prevent rotation thereof. The tens housing feature comprises one or more axially forwardly extending formations 108 which may be equally spaced around the internal circumference of the housing 112. The formations 108 engage with corresponding axially rearwardly extending formations 119b at the rear of the tens wheel 119. The tens housing feature formations 108 and the tens wheel formations 119b may be teeth, notches, castellations or any other shaped formations that, when engaged together, prevent relative rotation between the tens wheel 119 and the housing 112.

An internal surface of the housing 112 is provided with a units housing feature 107 capable of moving the units wheel axially-forward against said biasing means 117. The units housing feature is an axially forwardly extending formation 107 having a cam surface which can engage with an axially rearwardly extending formation 118b on the units wheel 118 in order to push the units wheel 118 axially forwards.

Teeth 118a on the front end of the units wheel 118 are engageable with correspondingly shaped teeth 119a at the rear end of the tens wheel 119. On the tens wheel 119, the teeth 119a (for engaging the units wheel) and the tens wheel formations 119b (for engaging the housing) may be concentrically arranged around the longitudinal axis of the injection device, with the teeth 119a radially inward of the formations 119b.

The drive spring 120 is a torsion spring which is fixed at one end with respect to the housing 112 and rotationally coupled at its other end to the drive shaft 140 via the units wheel 118.

A worm gear arrangement is provided which comprises a worm gear 142 meshed with a toothed plunger rack 145 located within the housing 112. During dose delivery, the worm gear 142 drives the plunger rack 145 forward which, in turn, pushes against the cartridge stopper 126 to deliver a dose of medicament. A splined clutch 150 at the forward end of the drive shaft 140 enables the worm gear 142 and drive shaft 140 to be splined together during dose delivery but not during dose setting and this will be described in more detail later. In FIG. 6, the worm gear rotational lock 144 is engaged in the forward end of the worm gear 142, preventing rotation thereof. The worm gear rotational lock 144 is capable of being pushed axially forward by the drive shaft 140 in order to disengage the lock from the worm gear 142.

The dose limit nut 141 is keyed to the drive shaft 140 so that they are rotationally coupled but not axially coupled. The dose limit nut 141 is engaged with the teeth of the plunger rack 145 and can travel axially forward and backward along the plunger rack 145 as the dose is incremented or decremented respectively. The axial range within which the dose limit nut 141 can travel along the plunger rack 145 is determined by dose limit nut endstop features 141a, 141b which can engage features 147, 148 on the plunger rack thread to serve as endstops for the travel of the dose limit nut 141. FIG. 5A shows the maximum dose limit nut endstop feature 141a and the minimum dose limit nut endstop feature 141b in more detail. Endstops 141a, 141b are able to engage features 147, 148 respectively on the plunger rack 145 (FIG. 5B). These features 147, 148 are preferably changes in the depth of or formations on the plunger rack thread, past which the dose limit nut 141 cannot travel. During dose delivery, the dose limit nut 141 rotates about axis L with the drive shaft 140 to which it is keyed, but it does not move axially with respect to the plunger rack 145 with which it is engaged, thus always keeping the dose limit nut 141 within the range defined by the max/min dose endstops 141a, 141b.

The operation of the respective features of the injection device 100 will now be described in more detail below.

Dose Setting—Incrementing the Dose

Figure 7:
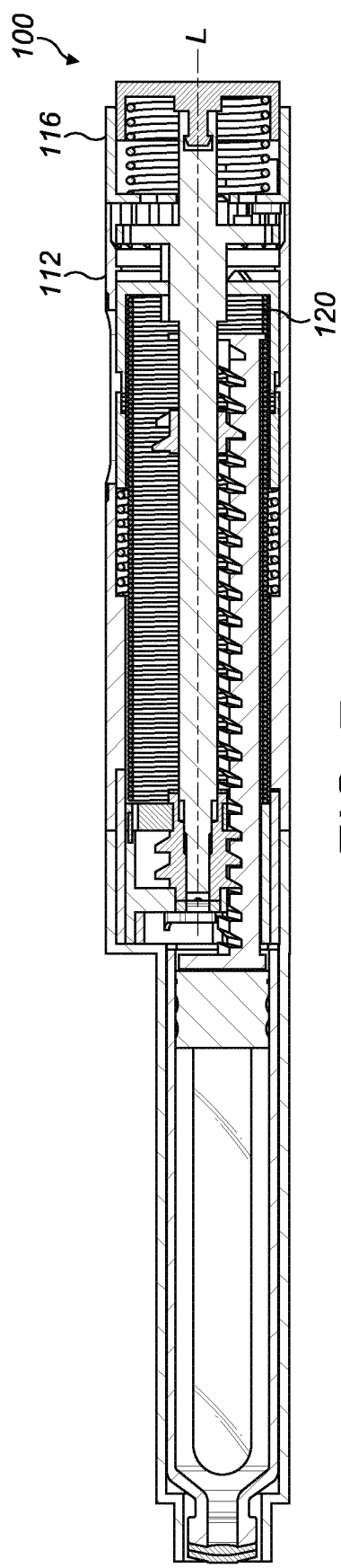
FIGS. 7 and 7A-7C illustrate incrementing the dose.
Figure 7C:
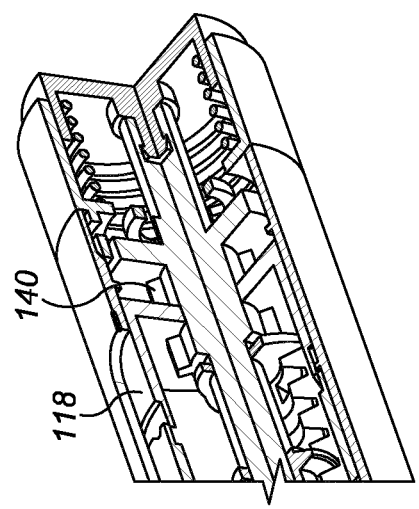

With the injection device 100 in the configuration shown in FIG. 7, the user grips the dose selector 116 and rotates it clockwise about axis L, with respect to the housing 112, in order to increment the dose and charge the drive spring 120. As the dose selector 116 is turned clockwise, the pawl features 115 engaging the splines 149 on the drive shaft 140 cause the drive shaft 140 to also be driven clockwise, as shown in FIG. 7A.

Figure 7B:
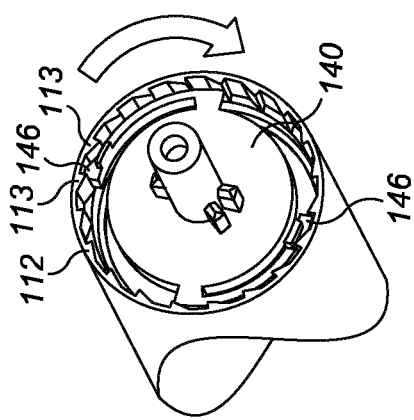
Figure 7A:
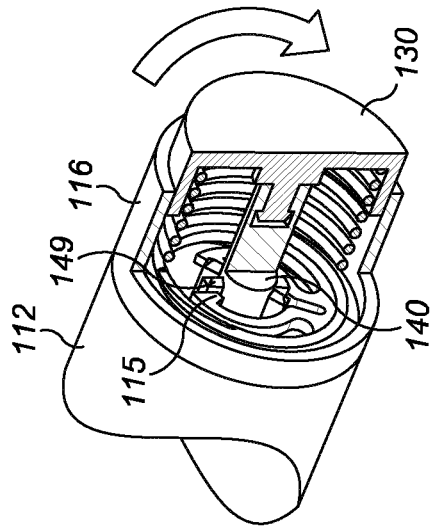
Figure 8:
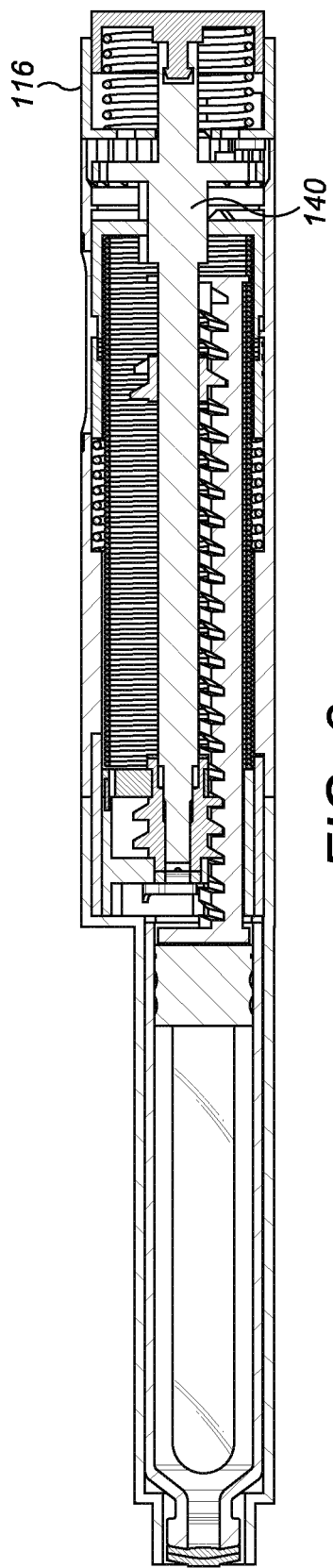
FIGS. 8, 8A and 8B illustrate decrementing the dose.
Figure 8B:
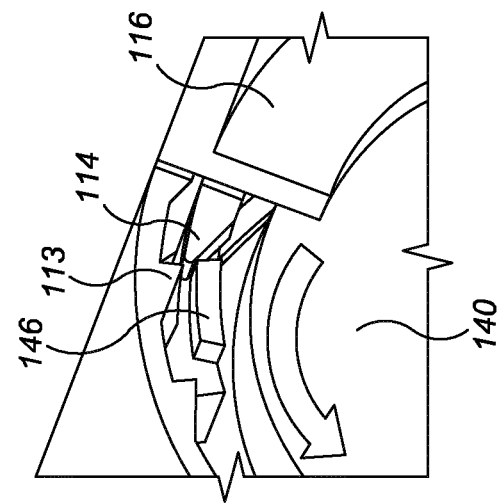

While the dose is being incremented, the ratchet arms 146 on the drive shaft 140 engage with the teeth 113 on the inside surface of the housing 112 to prevent un-winding by the drive spring 120, as shown in FIG. 7B.

As shown in FIG. 7C, the drive shaft 140 is splined to the units wheel 118 which charges or torques up the drive spring 120. In other words, torque is transferred from the dose selector 116 to the drive spring 120 directly through the dose indicator, i.e. the units wheel 118.

Dose Setting—Decrementing the Dose

Figure 8A:
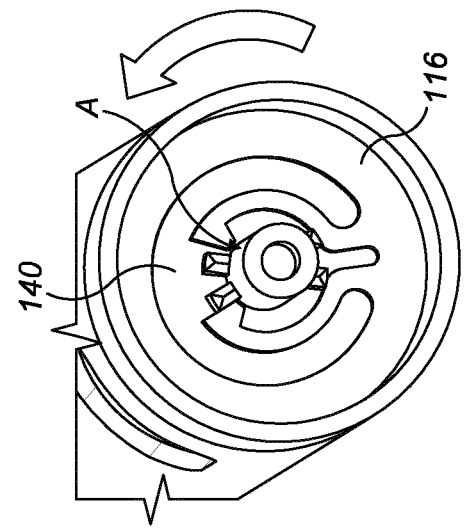

When it is desired to decrement the selected dose, the dose selector 116 is turned anti-clockwise. As shown in FIG. 8A, as the dose selector 116 is turned anti-clockwise, there is a small amount of backlash at point A such that the dose selector 116 can rotate slightly with respect to the drive shaft 140. This small relative movement is sufficient to allow the tabs 114 on the dose selector 116 to depress the drive shaft ratchet arms 146 so that they can click past the housing teeth 113, allowing the drive spring to unwind slightly before the ratchet arms 146 catch again on the next housing tooth 113. This is represented in FIG. 8B. Each decrement preferably equates to 1IU ("international unit") of medicament.

Dose Setting—Maximum/Minimum Dose

Figure 9:
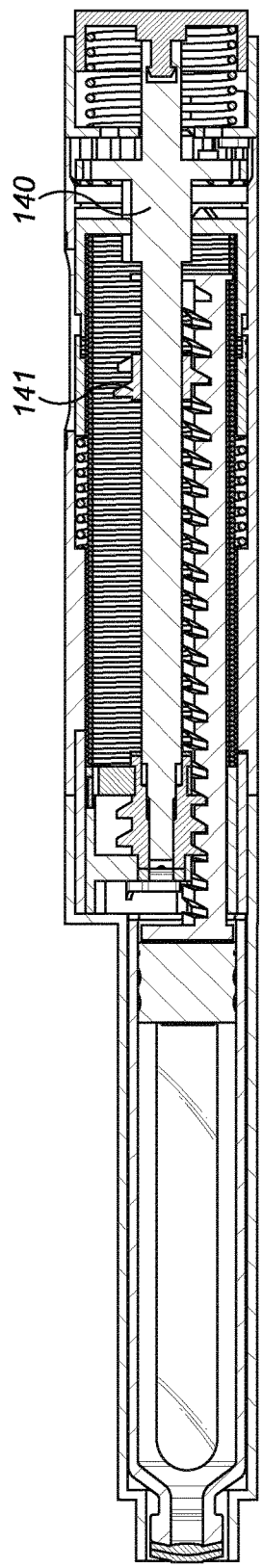
FIGS. 9, and 9A-9D illustrate maximum/minimum dose limiting.
Figure 9C:
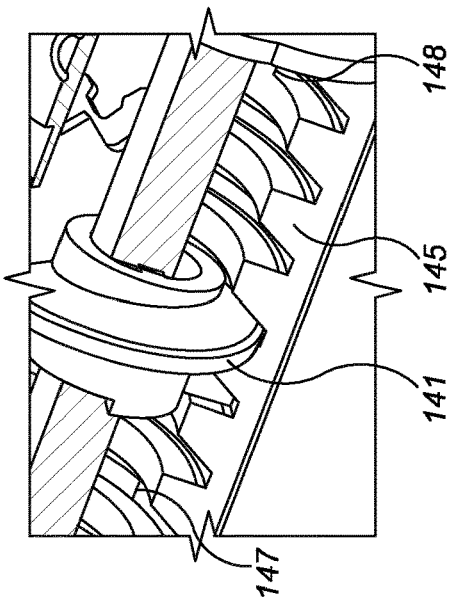
Figure 9B:
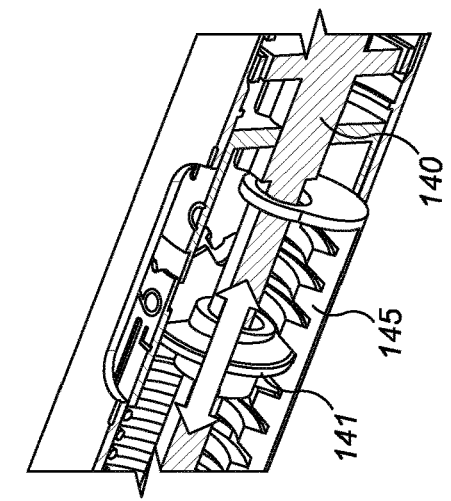
Figure 9A:
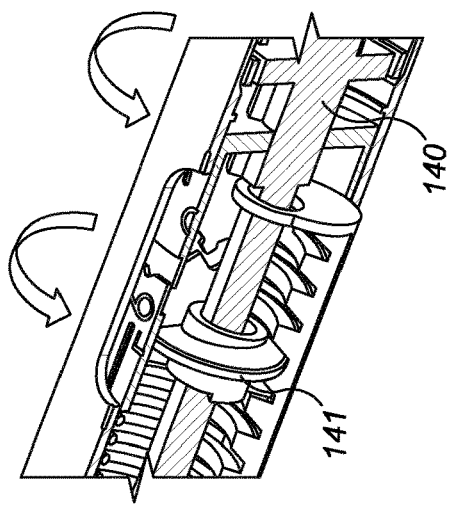
Figure 9D:
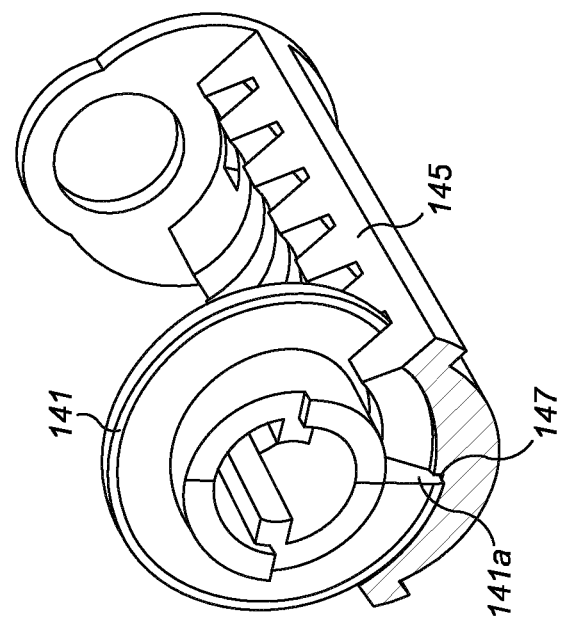

As the drive shaft 140 is rotated during dose setting, the dose limit nut 141, which is keyed to the drive shaft 140, is also rotated (FIG. 9A). The dose limit nut 141 travels forwards when incrementing the dose and rearwards when decrementing the dose (FIG. 9B). The dose limit nut 141 is engaged in the thread of the plunger rack 145. Endstop features 147, 148 are located on the plunger rack 145, past which the dose limit nut 141 cannot travel (FIG. 9C). These endstop features 147, 148 may be changes in the depth of the thread. As shown in FIG. 9D, when the dose limit nut 141 rotates into a position wherein the dose limit nut endstop feature 141a engages feature 147 on the plunger rack 145, further rotation of the dose limit nut 141 is prevented so that a dose of medicament greater than the desired maximum dose of medicament cannot be set. Limiting the travel of the dose limit nut 141 sets the maximum and minimum doses of medicament that can be set during dose setting, preferably 100 IU and 0 IU respectively.

Dose Setting—Over Torque

Figure 10:
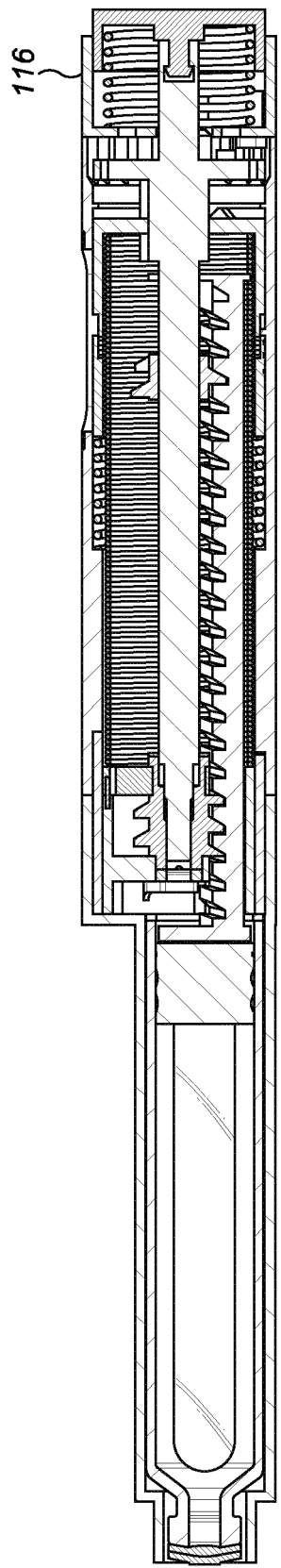
FIGS. 10 and 10A illustrate over-torque protection.
Figure 10A:
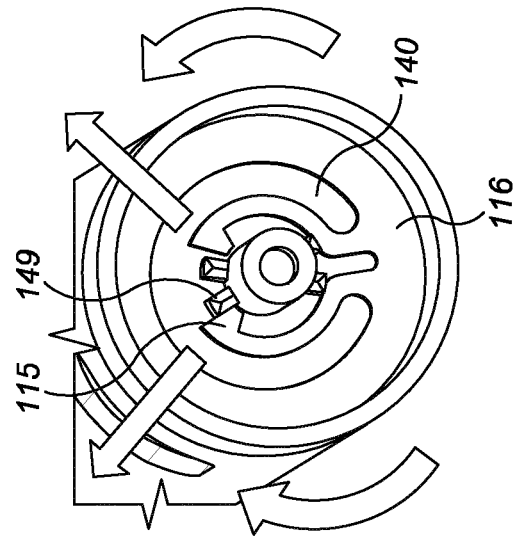

As shown in FIG. 10A, in the event the user applies too much force (over torque) to the dose selector 116 in either rotational direction, the dose selector pawl features 115 will flex radially outwardly to allow them to skip past splines 149 on the drive shaft 140. Preferably the interfacing surface areas of the pawl features 115 and/or splines 149 act as a cam lever, preferably having a matching angle and/or a defined static and dynamic surface friction at the interface surface. The over-torque for flexing out the dose pawl features 115 to skip past spline 149 is preferably at least 10% higher than the torque required for dialling up (incrementing) or dialling down (decrementing) the dose indicator 18, 118. The dialling up torque can be 30 to 80 Nmm, preferably less than 60 Nmm, more preferably 30 to 50 Nmm. The dialling down torque can be 20 to 60 Nmm, preferably less than 50 Nmm, more preferably 30 to 40 Nmm. The over-torque in the dialling up direction may be different to the over-torque in dialling down direction. The outward flexing force and/or strength of one flexible pawl arm 115 could be lower compared to a second flexible pawl arm.

Figure 16:
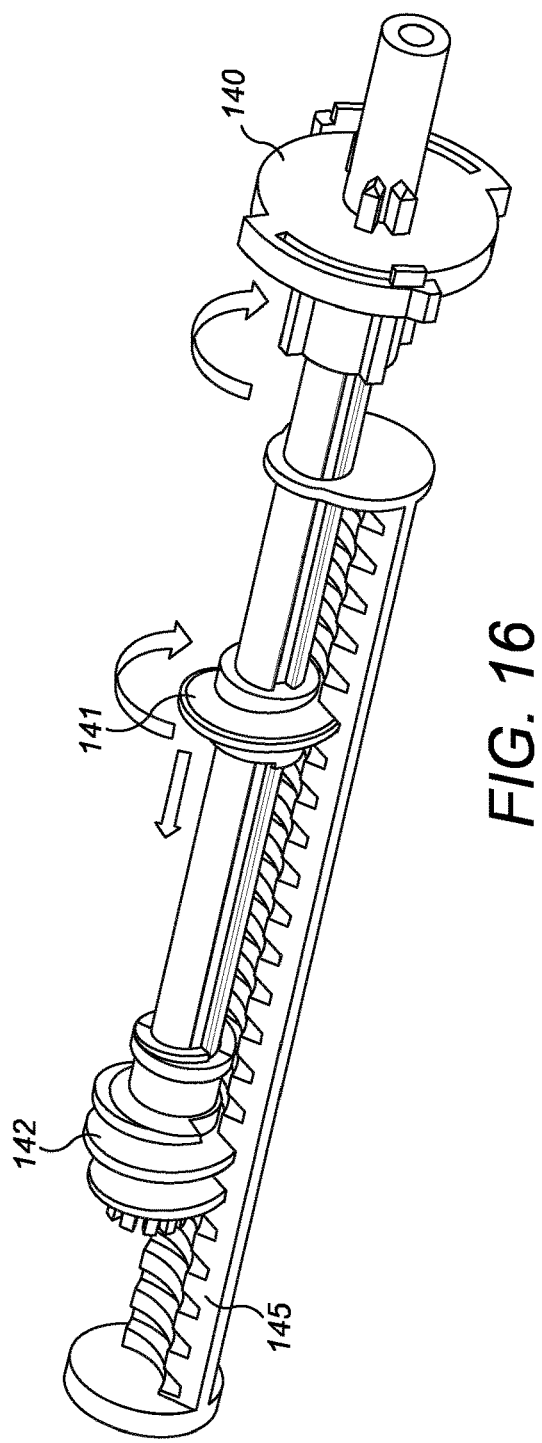
FIG. 16 summarises schematically the mechanical motion of the drive shaft 140, dose limit nut 141, worm gear 142 and plunger rack 145 during dose setting (incrementing the dose)

FIG. 16 summarises schematically the mechanical motion of the drive shaft 140, dose limit nut 141, worm gear 142 and plunger rack 145 during dose setting (incrementing the dose). The drive shaft 140 rotates clockwise. The dose limit nut 141 rotates clockwise and advances forwards with respect to the plunger rack 145.

Dose Delivery

Figure 11:
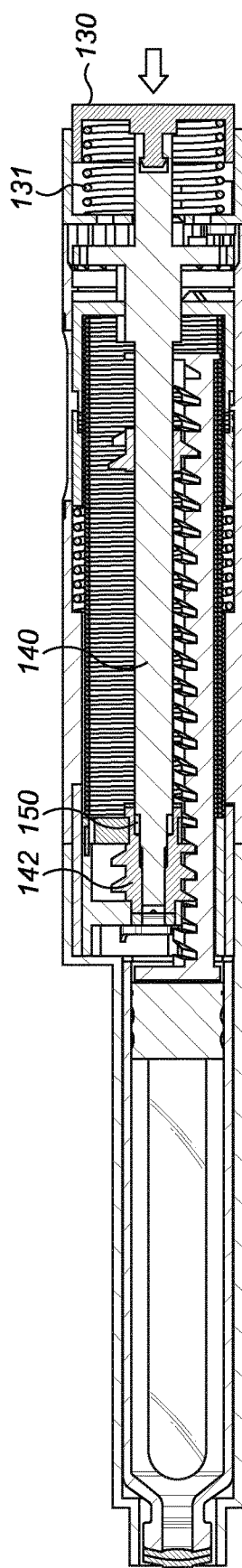
Figure 11C:
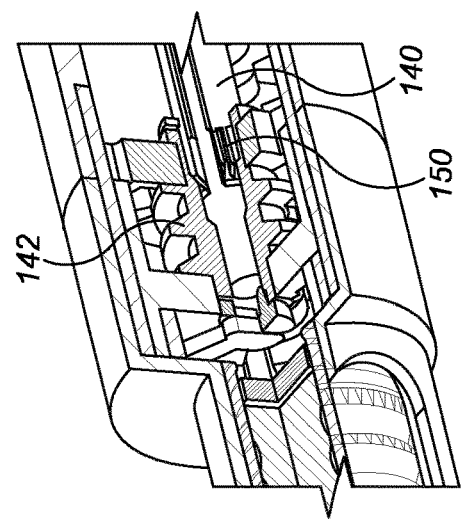
Figure 11B:
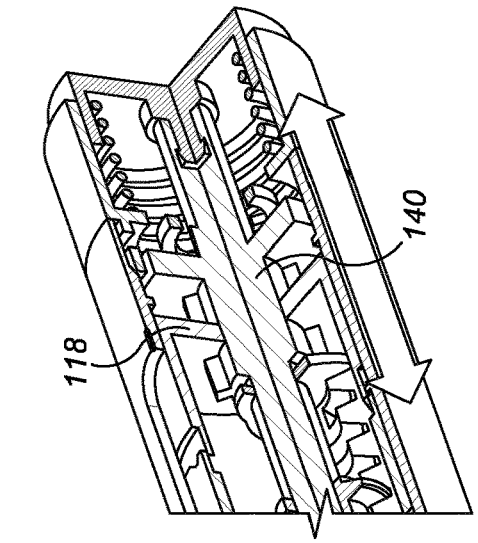
Figure 11A:
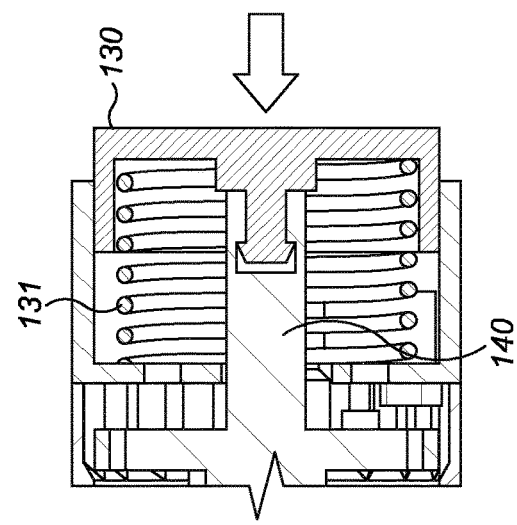

To initiate dose delivery, the user presses the dose button 130 against the bias of the dose button spring 131 as shown in FIG. 11A. This pushes the drive shaft 140 axially forwards. Although the drive shaft 140 is splined to the units wheel 118, it is free to slide axially with respect thereto (FIG. 11B).

Figure 12:
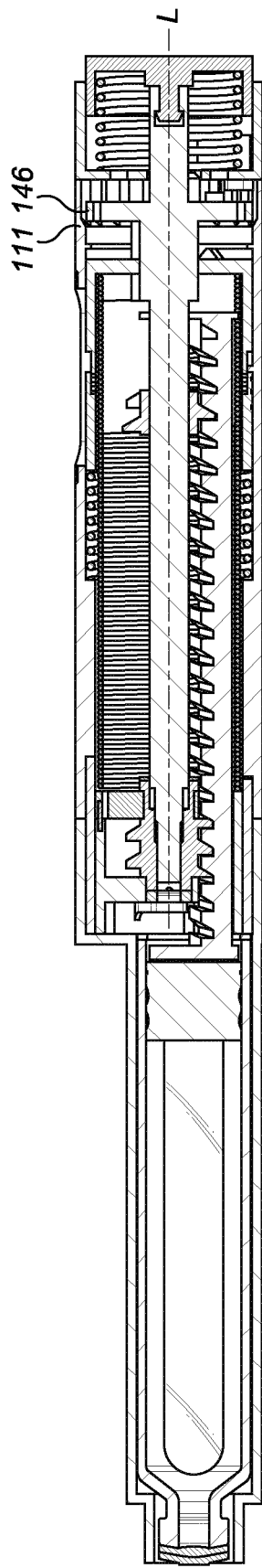
Figure 12B:
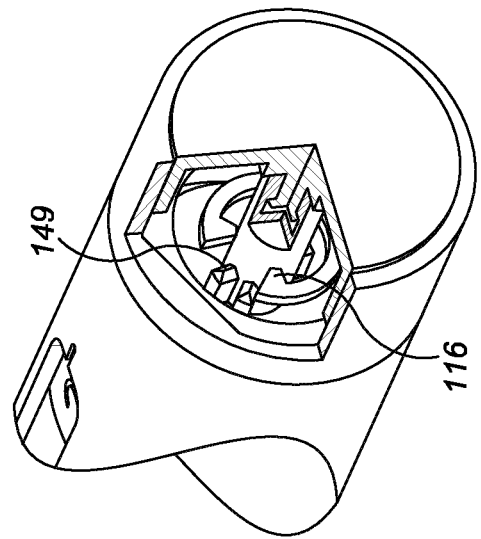
Figure 12A:
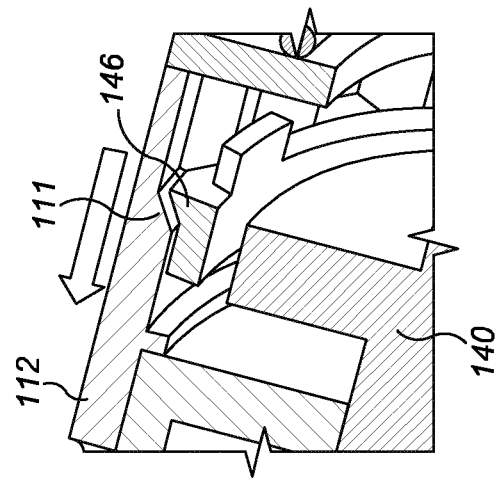

As the drive shaft 140 advances, at its forward end, the splined clutch 150 between the drive shaft and the worm gear 142 engages (FIG. 11O, FIG. 15—Worm Gear Clutch 150). Preferably the drive element, in particular the worm gear 142 and the drive shaft 140 engage after 0.5 mm to 1.5 mm advancement of the dose button 130, more preferably after 0.8 mm to 1.2 mm advancement of the dose button 130. Once the clutch 150 has started to engage, the ratchet arms 146 on the drive shaft 140 begin to disengage from the inside surface of the housing 112 aided by ramp features 111 (FIG. 12A, FIG. 15—Hold Ratchet). Preferably the hold ratchet, in particular the ratchet arms 146 on the drive shaft 140 start to disengage from the structured, in particular toothed surface of the housing 112 after 1.5 mm to 2.5 mm advancement of the dose button 130, more preferably after 1.6 mm to 1.9 mm advancement of the dose button 130. Also, as the drive shaft 140 moves forward, the splines 149 coupling the drive shaft 140 to the dose selector 116 disengage (FIG. 12B, FIG. 15—Over torque ratchet). Preferably the over torque ratchet, in particular the drive shaft splines 149 on the drive shaft 140 start to disengage from the dose selector pawls 115 after 1.5 mm to 3.5 mm of advancement of the dose button 130, more preferably after 2 mm to 3 mm advancement of the dose button 130. The dose indicator and drive shaft 140 are now free to rotate about longitudinal axis L.

The drive spring 120 drives the units wheel 118 to rotate about longitudinal axis L. The units wheel 118 drives the drive shaft 140 which drives the worm gear 142.

Figure 17:
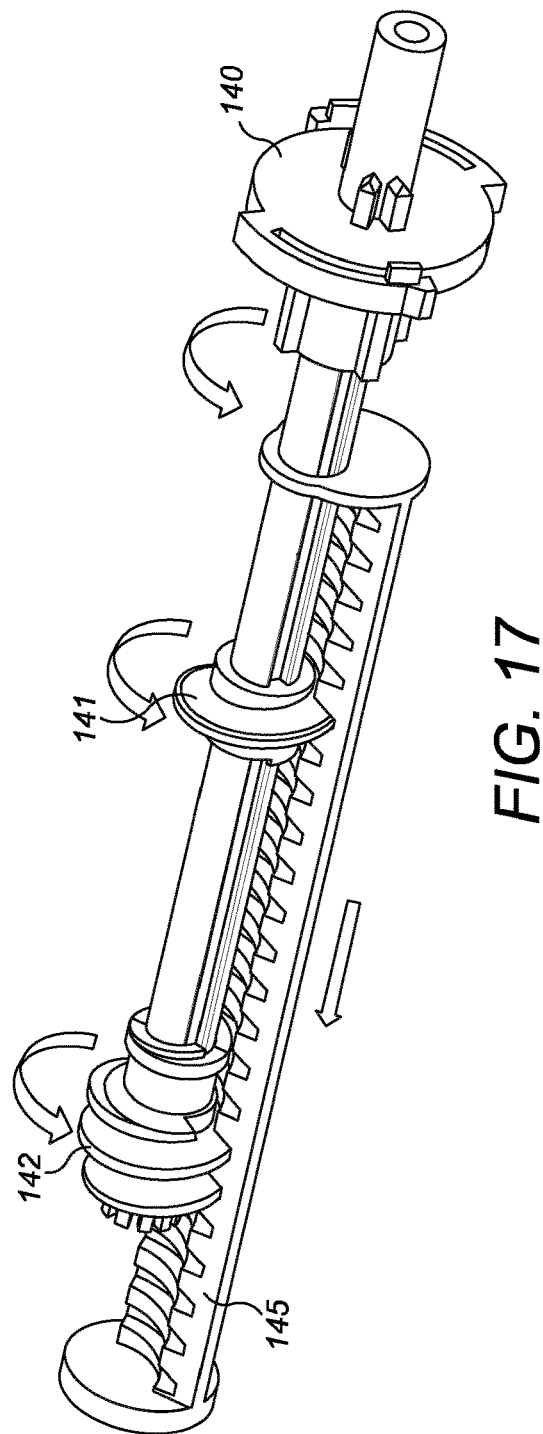
FIG. 17 summarises schematically the mechanical motion of the drive shaft 140, dose limit nut 141, worm gear 142 and plunger rack 145 during dose delivery.

FIG. 17 summarises schematically the mechanical motion of the drive shaft 140, dose limit nut 141, worm gear 142 and plunger rack 145 during dose delivery. The drive shaft 140, dose limit nut 141 and worm gear 142 all rotate anti-clockwise. Only the plunger rack 145 advances forwards. During dose delivery, the dose limit nut 141 rotates with the drive shaft 140 but does not move axially with the plunger rack 145. The dose limit nut 141 and the drive worm gear 142 preferably have the same thread pitch.

The worm gear 142 actuates the plunger rack 145 to move axially forwards causing the cartridge stopper 126 to be driven into the cartridge in order to expel medicament thus delivering the selected dose.

When the dose button 130 is released, the dose button spring 131 returns the dose button 130 and drive shaft 140 to their original starting positions. This axially rearward movement disengages the worm gear clutch 150 and re-engages the drive shaft ratchet arms 146 with the housing 112 thereby stopping dose delivery.

Dose Delivery—Haptic Feedback

During dose delivery, the drive shaft ratchet arms 146 run (rotationally) on a relatively smooth track 110 on the inside surface of the housing 112 (FIG. 13A). Optionally, this track could be modified to include ridges 109 which would provide audible/haptic feedback to the user during dose delivery (FIG. 13B). The ridges 109 are conveniently placed relatively close to the user's fingers.

Last Dose Protection

When the medicament cartridge 124 is relatively empty, after several doses have already been delivered therefrom, it is undesirable for the user to be able to select a dose that is larger than the available quantity of medicament remaining. Last dose protection is provided to deal with this situation. Conveniently, the last dose protection is provided by the same feature as the max/min dose limiting i.e. the dose limit nut 141.

As shown in FIG. 14, after several doses have been delivered, the plunger rack 145 and dose limit nut 141 have advanced axially forwards such that the dose limit nut 141 is approaching the worm gear 142. When there is less than a predetermined amount (e.g. 100 IU) of medicament available, the worm gear 142 serves as an endstop, stopping the dose limit nut 141 from moving further forwards and before the maximum dose limit feature 147 on the plunger rack 145 is reached (FIG. 14A). Preferably, it is the dose limit nut endstop feature for maximum dose limiting 141a which engages the worm gear 142. If the user tries to increment the dose further, torque is transmitted through the dose limit nut 141 into the worm gear 142, the torque being reacted to by the worm gear rotational lock 144 (FIG. 14B). As such, the worm gear 142 is unable to rotate due to rotational engagement with the rotational lock 144.

Figure 14C:
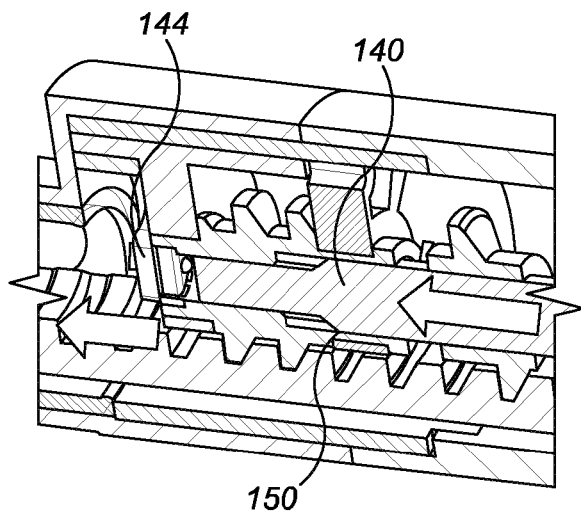
Figure 14D:
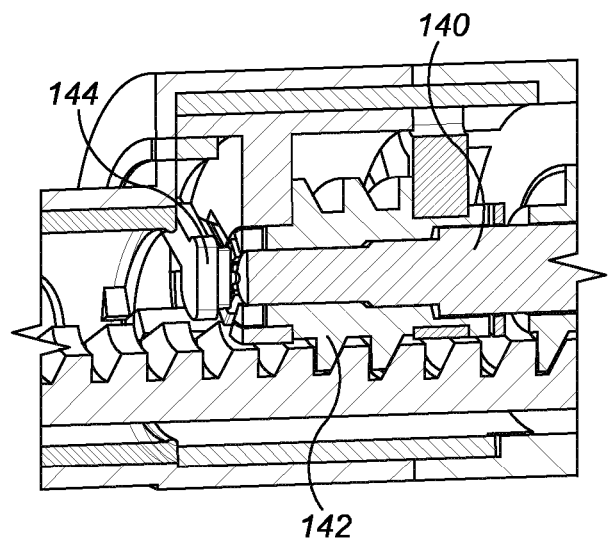
Figure 14E:
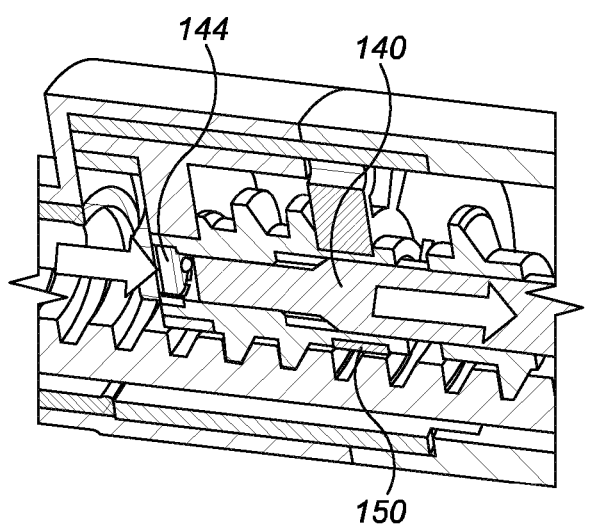

During dose delivery, when the drive shaft 140 is moved axially forwards, the worm gear clutch 150 is engaged before the worm gear rotational lock 144 is disengaged (FIG. 14C). The axially-forward movement of the drive shaft 140 causes its forward end to push the worm gear rotational lock 144 out of the front of the worm gear 142. With the worm gear rotational lock 144 disengaged, the worm gear 142 is free to rotate, driven by the drive shaft 140 (FIG. 14D). Once dose delivery is finished, the drive shaft 140 moves rearwardly. The worm gear rotational lock 144 re-engages, before the worm gear clutch 150 is disengaged (FIG. 14E).

FIG. 15 is a diagrammatic summary of the key engagement points of the injection device components, at four stages of dose delivery.

Dose Display

Figure 18:
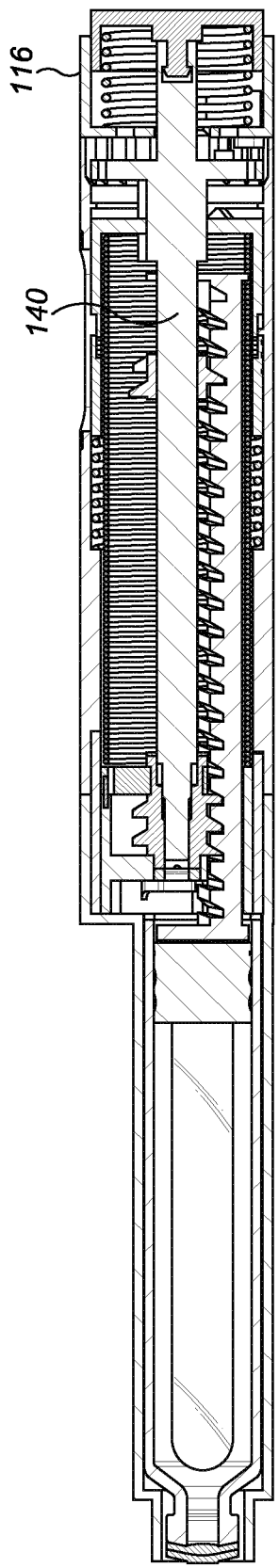
FIGS. 18, 18A and 18B show how the units wheel is incremented.
Figure 18B:
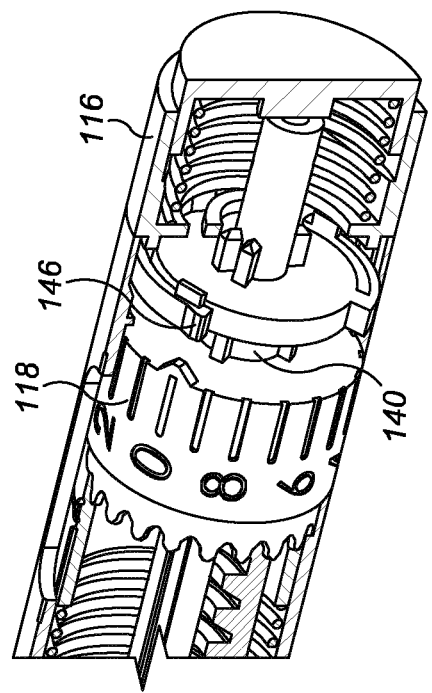
Figure 18A:
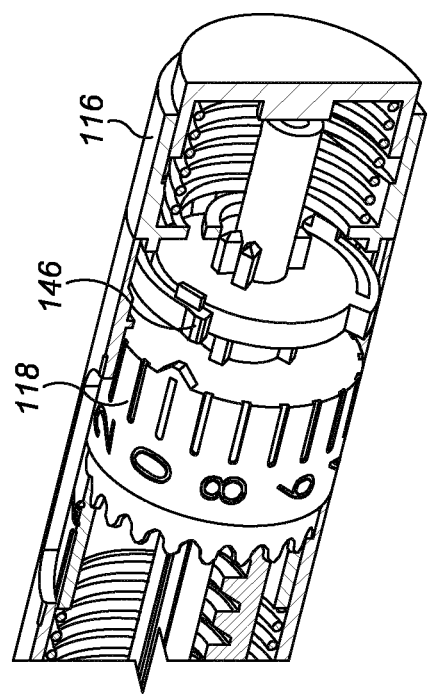

As already described above, during dose selection the user rotates the dose selector 116 which also drives the drive shaft 140 around. Ratchet arms 146 interact with teeth 113 in the housing 112 to prevent unwinding (FIG. 18A). The drive shaft 140 is splined to the units wheel 118 which, as it turns, increments the displayed unit (FIG. 18B).

Figure 19:
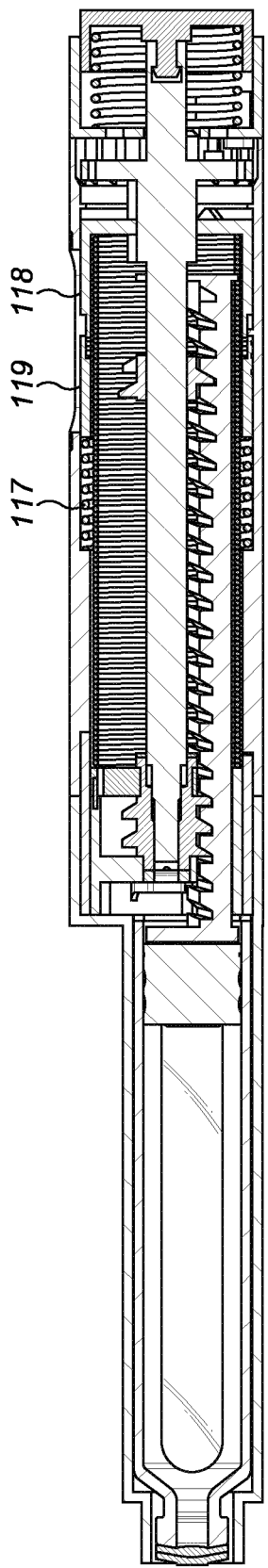
FIGS. 19, 19A and 19B show how the tens wheel is incremented.
Figure 19B:
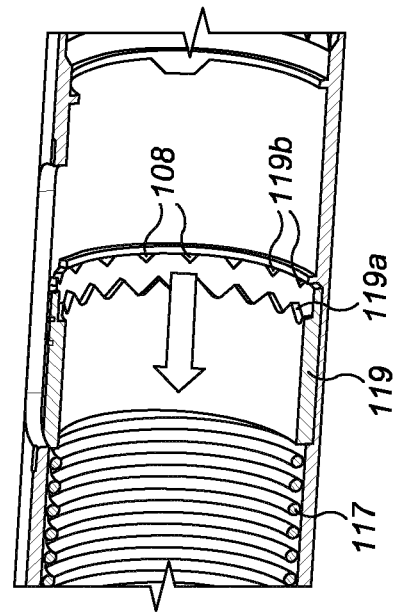
Figure 19A:
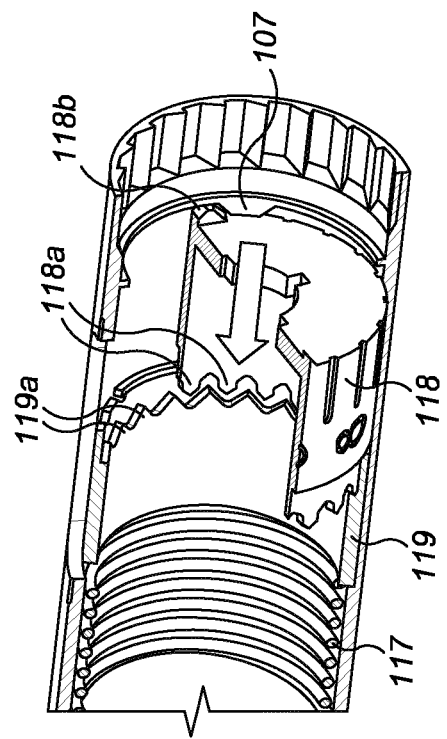

The units wheel 118 and tens wheel 119 are biased rearwardly by dose indicator spring 117. Twice per revolution of the units wheel 118, the units wheel 118 is moved axially forwards by the cam surface of the units housing feature 107 engaging with the formation 118b on the units wheel 118. This axially forward movement causes the teeth 118a of the units wheel 118 to engage with the teeth 119a of the tens wheel 119 (FIG. 19A). Continued forward axial movement of the units wheel 118 pushes the formations 119b of the tens wheel 119 away from the tens housing feature 108, so that the tens wheel 119 is free to rotate with respect to the housing 112, allowing the tens wheel 119 to be driven around by the units wheel 118 by one increment (FIG. 19B).

As with the first embodiment, described with reference to FIGS. 1-3, biasing means in the form of dose indicator spring 117 biases the units wheel 118 and tens wheel 119 axially rearwardly in the housing.

An internal surface of the housing 112 is provided with a tens housing feature 108 selectively engageable with the tens wheel 119 to prevent rotation thereof.

An internal surface of the housing 112 is provided with a units housing feature 107 capable of moving the units wheel axially-forward against said biasing means 117 such that the units wheel 118 engages and moves the tens wheel 119 axially-forward and free of said tens housing feature 108 so as to allow rotation thereof.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 7 units housing feature
8 tens housing feature
10 injection device
L longitudinal axis
10a front end of the device
10b rear end of the device
12 housing
12a aperture in the housing
14 needle
16 dose selector
17 dose indicator spring
18 units wheel of dose indicator
18a teeth on units wheel
19a teeth on tens wheel
19 tens wheel of dose indicator
100 injection device
L longitudinal axis (housing)
Lc second longitudinal axis (cartridge)
100a front end of the device
100b rear end of the device
107 units housing feature
108 tens housing feature
109 housing ridge features
110 housing smooth inside surface track
111 housing ramps for drive shaft ratchet arms
112 housing
112a aperture in the housing
113 housing teeth
114 tabs
115 dose selector pawl
116 dose selector
117 dose indicator spring
118 units wheel
118a teeth on units wheel (for engaging tens wheel)
118b formation on units wheel (for engaging units housing feature)
119 tens wheel
119a teeth on tens wheel (for engaging units wheel)
119b formations on tens wheel (for engaging tens housing feature)
120 drive spring
124 medicament cartridge
125 cartridge holder
126 cartridge stopper
130 dose button
131 dose button spring
140 drive shaft
141 dose limit nut
141a dose limit nut endstop feature for max dose limiting and last dose limiting
141b dose limit nut endstop feature for min dose limiting
142 worm gear
143 worm gear support 144 worm gear rotational lock
145 plunger rack
146 drive shaft ratchet arms
147 max dose endstop on plunger rack for dose limit nut
148 min dose endstop on plunger rack for dose limit nut
149 drive shaft splines
150 worm gear clutch
A backlash point for over-torque protection

The invention claimed is:

1. An injection device comprising:
   a. a housing having a longitudinal axis;
   b. a dose selector capable of setting a dose to be ejected from the injection device;
   c. a dose indicator comprising a units wheel operatively connectable to the dose selector so that rotation of the dose selector about the longitudinal axis also rotates the units wheel, and a tens wheel selectively engageable with the units wheel so that rotation of the units wheel also rotates the tens wheel; and
   d. a biasing means for biasing the dose indicator axially-rearwardly in the housing,
   wherein an internal surface of the housing is provided with a tens housing feature comprising one or more formations selectively engageable with corresponding features on the tens wheel to prevent rotation thereof,
   and wherein the internal surface of the housing is provided with a units housing feature capable of moving the units wheel axially-forward against said biasing means such that the units wheel engages and moves the tens wheel axially-forward and free of said tens housing feature so as to allow rotation thereof.

2. The injection device of claim 1 wherein the biasing means is a spring.

3. The injection device of claim 1 wherein the units housing feature comprises a cam surface.

4. The injection device of claim 3 wherein the units wheel comprises an axially-rearwardly-extending formation for engaging said cam surface on the housing.

5. The injection device of claim 1 wherein said units wheel is selectively engageable with said tens wheel by means of one or more teeth on the units wheel engageable with corresponding teeth on said tens wheel.

6. The injection device of claim 5 wherein said formations and/or teeth are regularly spaced.

7. The injection device of claim 5 wherein said formations and/or teeth on the tens wheel are located at a rear end of said tens wheel.

8. The injection device of claim 5 wherein said tens wheel teeth for engaging the units wheel are located radially inwardly of the tens wheel formations for engaging the tens housing feature.

9. The injection device of claim 1 wherein the dose indicator is arranged concentrically about said longitudinal axis.

10. The injection device of claim 1 further comprising a medicament container.

11. The injection device of claim 10 wherein the medicament container comprises a pre-filled syringe or cartridge.

12. The injection device of claim 10 further comprising a medicament contained in the medicament container.

13. The injection device of claim 12 wherein the medicament is selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

* * * * *